(12) United States Patent
Joslyn

(10) Patent No.: US 6,656,423 B1
(45) Date of Patent: Dec. 2, 2003

(54) STERILE WATER GENERATOR

(75) Inventor: Larry J. Joslyn, Mentor, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/498,864

(22) Filed: Feb. 7, 2000

(51) Int. Cl.$^7$ ................................................ C02F 1/02
(52) U.S. Cl. ........................... 422/1; 422/28; 422/292; 422/298; 210/175
(58) Field of Search ................................ 134/60, 100.1; 210/175, 1, 28, 292, 295; 422/296, 1

(56) References Cited

U.S. PATENT DOCUMENTS

| | | | |
|---|---|---|---|
| 4,281,674 A | * | 8/1981 | Tanaka et al. ............... 134/95.2 |
| 4,337,223 A | | 6/1982 | Kaye ........................... 422/112 |
| 4,637,916 A | | 1/1987 | Hennebert et al. ............. 422/36 |
| 4,731,222 A | * | 3/1988 | Kralovic et al. ............... 422/37 |
| 4,764,351 A | | 8/1988 | Hennebert et al. ........... 422/292 |
| 4,892,706 A | | 1/1990 | Kralovic et al. .............. 422/28 |
| 5,209,909 A | | 5/1993 | Siegel et al. |
| 5,217,698 A | * | 6/1993 | Siegel et al. ................. 422/295 |
| 5,223,217 A | | 6/1993 | Frizziero ...................... 422/26 |
| 5,268,144 A | | 12/1993 | Heilmann et al. ............. 422/26 |
| 5,279,799 A | | 1/1994 | Moser |
| 5,348,711 A | * | 9/1994 | Johnson et al. .............. 422/300 |
| 5,556,607 A | | 9/1996 | Childers et al. .............. 422/360 |
| 5,558,841 A | | 9/1996 | Nakagawa et al. |
| 5,562,882 A | | 10/1996 | Smith et al. .................. 422/26 |
| 5,589,005 A | | 12/1996 | Ohmi ............................ 134/30 |
| 5,753,195 A | | 5/1998 | Langford et al. |
| 5,830,409 A | | 11/1998 | Childers et al. ............... 422/30 |
| 5,858,305 A | | 1/1999 | Malchesky .................... 422/28 |
| 6,013,227 A | | 1/2000 | Lin et al. |
| 6,068,815 A | | 5/2000 | Oberleitner et al. |

FOREIGN PATENT DOCUMENTS

| | | | |
|---|---|---|---|
| DE | 40 03 987 | | 8/1991 |
| DE | 41 08 538 | | 9/1992 |
| EP | 0 323 654 | | 7/1989 |
| EP | 0 428 009 | | 5/1991 |
| EP | 0 514 636 | | 11/1992 |
| FR | 2627479 | * | 8/1989 |
| JP | 07265691 A | * | 10/1995 |

* cited by examiner

Primary Examiner—Robert J. Warden, Sr.
Assistant Examiner—Sean E. Conley
(74) Attorney, Agent, or Firm—Fay, Sharpe, Fagan, Minnich & McKee, LLP

(57) ABSTRACT

A sterile water generator (B) generates a stream of sterile water on demand. A water heater (130) heats incoming, unsterile water to a sufficient temperature to achieve sterilization of the water. The sterile water is then passed through a heat exchanger (110) which transfers excess heat from the sterile water to the incoming water. This reduces the energy consumption of the water heater and reduces the temperature of the sterile water ready for use. The sterile water is delivered to a site (A), at which the water is to be used, through a sterile water delivery pathway (C) to avoid recontamination of the water. A first portion (162) of the pathway is pre-sterilized by flowing steam or hot water, generated by the water heater, along the pathway (C). A second portion (212) of the pathway is sterilized with a liquid antimicrobial from the site. The first and second portions of the pathway have at least one common leg (164).

22 Claims, 5 Drawing Sheets

STERILE WATER GENERATOR

BACKGROUND OF THE INVENTION

The present invention relates to the generation and delivery of sterile water. It finds particular application in medical applications and in the decontamination arts. It should be appreciated, however, that the invention is also applicable to other systems where a source of sterile water is employed.

High purity water, which is free of microorganisms and other contaminants, is desirable for a variety of medical, scientific, and pharmaceutical applications, including the formulation of intravenous solutions, irrigation during surgery, rinsing of sterilized equipment, and the like.

Sterile water is used in hospitals to prepare various solutions for many other purposes. To avoid shipment of large quantities of these solutions, it is desirable to have a generator which supplies sterile water on site in the hospital, ready for the dilution of dehydrated formulations, as needed. For field emergency support applications, it is preferable that the sterile water generator be readily portable, and have a low power consumption.

In dental applications, water is used to feed dental handpieces, such as drills, or to supply mouth rinse devices. The supply lines to such equipment are often long, resulting in propagation of waterborne pathogens during periods of inactivity. Such pathogens may be harmful to patients, especially during invasive procedures. Accordingly, it is desirable that the water supplied to the devices be free of pathogens. An on-site sterile water generator which is capable of delivering sterile water on demand is thus desirable.

A variety of sterilization and disinfection processes include a rinse cycle for rinsing items, such as medical and pharmaceutical devices, and the like, after decontamination. Automated sterilization systems have been developed in which a premeasured dose of a decontaminant, such as peracetic acid or other strong oxidant, is circulated in solution through the system. Examples of such systems are disclosed in U.S. Pat. Nos. 4,892,706 and 5,217,698. Items to be decontaminated are inserted into a receiving tray of the system and a cartridge of concentrated decontaminant is inserted into a well of the system. As water flows through the system, the decontaminant is diluted and carried to the receiving tray. At the end of the decontamination cycle, the decontaminant solution is disposed of and a rinse fluid is circulated through the system to remove traces of the decontaminant, detergents, minerals, or other residue from the system and from the decontaminated items.

To avoid recontamination of the items, the rinse fluid is preferably free of microorganisms. Tap water may contain $10^3$ microorganisms/ml. Thus, rinsing the decontaminated items with tap water can lead to recontamination of the items. Filters are often used to remove particles down to about 0.2 microns in diameter. Such filters have been useful in removing harmful organisms. However, tap water may contain undesirable substances that are below 0.2 microns, such as dissolved minerals, organic based substances, volatile solvents, and other potentially toxic or otherwise undesirable substances. Additionally, it has recently been found that some water systems may even have live viruses, spores, or other living organisms below 0.2 microns in size.

Filter elements typically include a pleated material for filtering the particles from water. Once microbial growth propagates into the pleated region of the filter element, it is difficult to sterilize the element with liquid sterilizing agents on the filtered side, due to concentration gradients between the water supply side and chemicals on the filtered water side. Filtered material builds up on the filter and slows the flow rate of water through the filter. The filter is, therefore, replaced periodically. Contaminants tend to enter the filtered side during the replacement process. It is therefore desirable to sterilize in place the filter and associated piping after filter replacement.

The present invention provides a new and improved sterile water generator and a method for sterilizing and maintaining a sterile pathway, which overcome the above-referenced problems and others.

SUMMARY OF THE INVENTION

In accordance with one aspect of the present invention, a sterile water generator is provided. The generator includes a water heater which receives incoming water and heats the water to a sufficient temperature to sterilize the water and presterilize a pathway for delivering the sterile water from the water heater to a site at which the sterile water is to be used, the presterilized pathway being sterilized along at least a portion of its length by high temperature water or steam from the water heater.

In accordance with another aspect of the present invention, a method of supplying sterile water through a sterile fluid pathway is provided. A first sterilizing fluid is passed along a first portion of the sterile fluid pathway to effect sterilization. A liquid is heated to generate a second sterilizing fluid. The second sterilizing fluid is passed along at least a second portion of a fluid pathway to effect sterilization of the second portion of the pathway. The first and second portions have at least one common element over which both fluids pass. Sterile water is subsequently passed along the sterile fluid pathway.

In accordance with another aspect of the present invention, a method of decontamination is provided. The method includes contacting items to be decontaminated with a decontaminant fluid and contacting the decontaminated items with a rinse fluid, the rinse fluid including water which has been heated to a sufficient temperature to sterilize the water.

In accordance with another aspect of the present invention, a decontamination system is provided. The system includes a vessel for receiving items to be sterilized. A source of wan antimicrobial agent is connected with the vessel and supplies the antimicrobial agent to the vessel for decontaminating the items in the vessel. A sterile water generator is connected with the vessel and supplies sterile rinse water to the vessel for rinsing the decontaminated items.

One advantage of the present invention is that sterile water is generated in a short period of time following commencement of heating of incoming tap water.

Another advantage of the present invention is in the provision of injection quality sterile water.

Another advantage of the present invention resides in its energy efficiency. Heat used in sterilizing the water is reclaimed by the incoming tap water.

Yet another advantage of the present invention is that the fluid pathways between the generator and the system in which the water is to be used are sterilized or pasteurized with steam or heated sterile water prior to passage of the sterile water therethrough.

A further advantage of the present invention is that water hardness salts are changed into solid form minimizing deposition on items rinsed as an integral part of the water sterilization process in the sterile water generating system.

A still further advantage of the present invention is the provision of a sterile sampling port for verifying the sterility of sterile water generated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
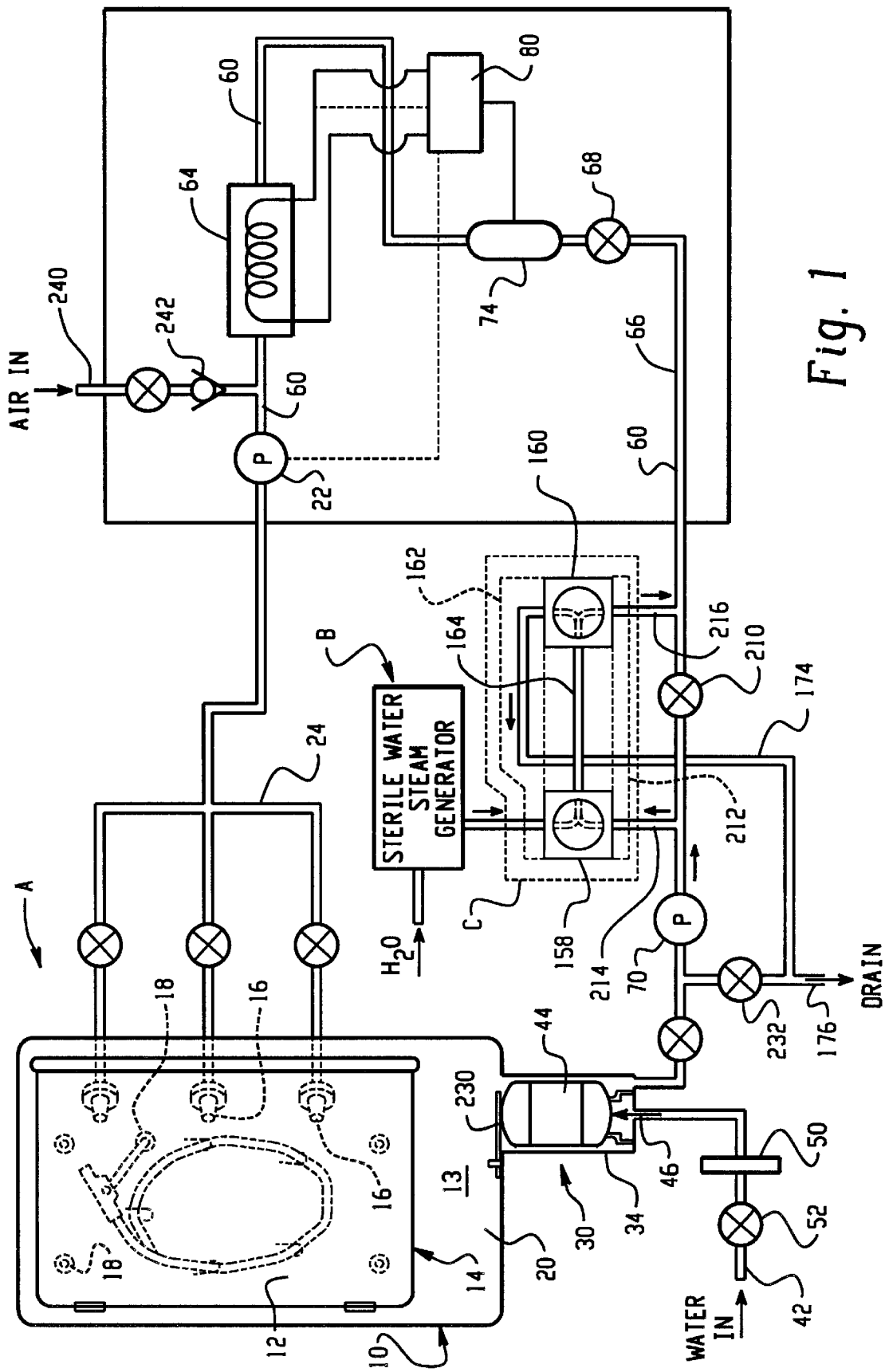
FIG. 1 is a plumbing diagram of a decontamination system employing a sterile water generator.
Figure 2:
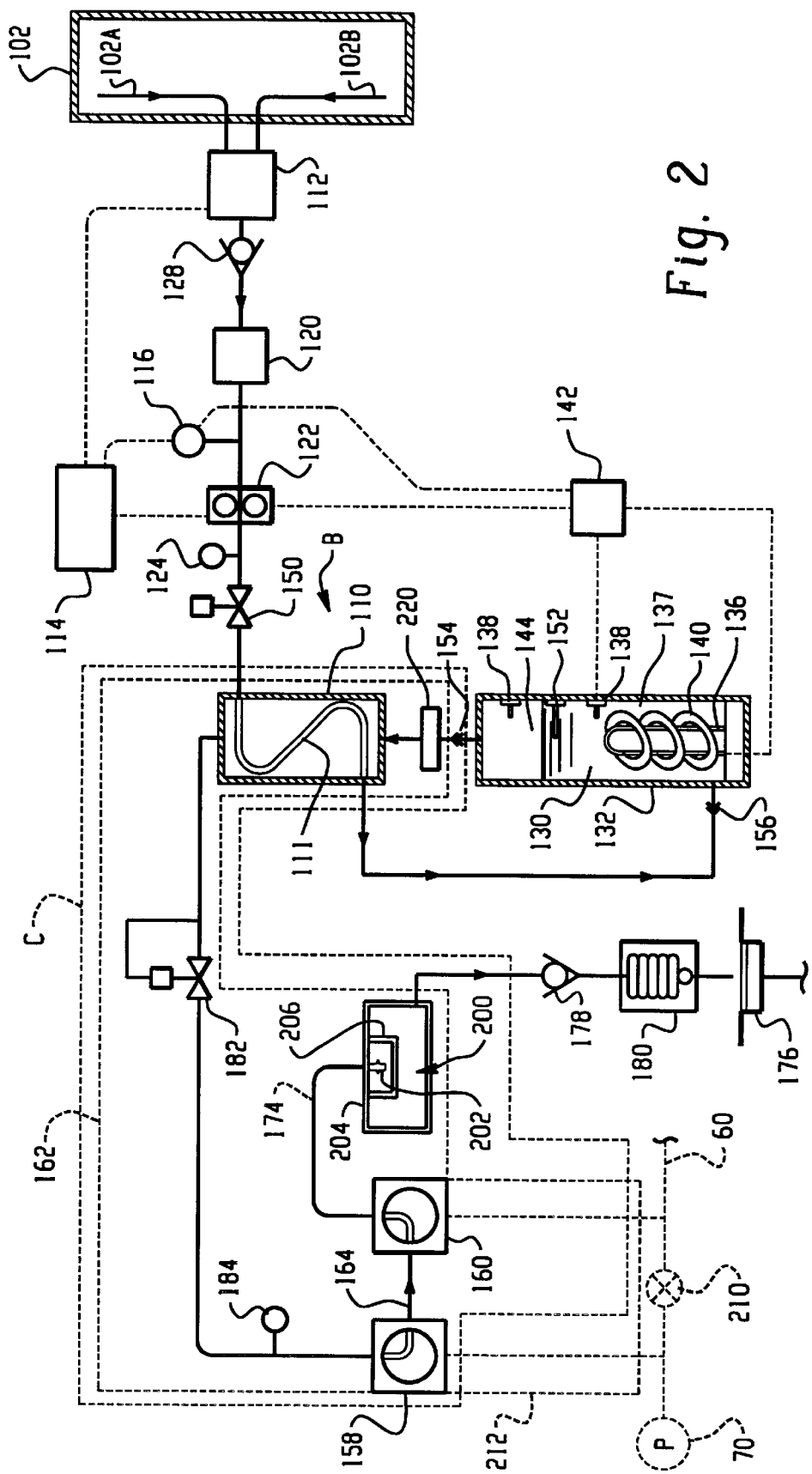
FIG. 2 is a plumbing diagram of a sterile water generator according to the present invention configured for supplying sterile water to a sampling and supplying steam for sterilization of internal fluid pathways.

With reference to FIG. 1, an automated liquid decontamination system A sanitizes, sterilizes, or disinfects items, such as medical, dental, and pharmaceutical devices, and the like. With reference also to FIG. 2, a sterile water generator B is coupled to the system A for providing sterile rinse water. The sterile rinse water is used to rinse the decontaminated items. It should be appreciated that the sterile water generator may be analogously connected to other systems in which a source of water which is free, or substantially free, of microorganisms, minerals, and other contaminants is desired.

The term "decontamination" and other terms relating to decontaminating will be used herein to describe sanitizing, sterilization, disinfection, and other antimicrobial treatments which are designed to remove and/or destroy microorganisms contaminating the items.

The system includes a decontamination cabinet 10 which defines an interior decontamination chamber 12. Items to be sterilized, disinfected, sanitized, or otherwise microbially decontaminated are loaded into the decontamination chamber through an opening in a front wall 13 of the cabinet, illustrated as closed by a door 14. Within the chamber, several spray jets or nozzles 16 spray a decontaminant solution over the items. Optionally, in the case of instruments with lumens, or other internal passages, some of the nozzles act as fluid ports 18 which are configured for interconnection with internal passages of the endoscopes and other objects with lumens, for supplying decontaminant solution and other liquids to the internal passages.

A collection tank or sump 20 forms the base of the cabinet 10 and receives the sprayed decontaminant solution as it drips off the items. A high pressure pump 22 delivers the decontaminant solution under pressure to the nozzles 16 and fluid ports 18 through a fluid distribution system 24.

A source 30 of a decontaminant solution preferably includes a well or mixing chamber 34. The well receives a dose of a concentrated decontaminant, such as an antimicrobial agent or reagents which react to form an antimicrobial agent on mixing with water. As shown in FIG. 1, the well is integral with the collection tank 20 of the chamber, although a separate well is also contemplated.

A preferred antimicrobial agent is peracetic acid, either in concentrated liquid form, or as a reaction product of powdered reagents, such as acetyl salicylic acid and sodium perborate. A water inlet 42 supplies water, typically from a municipal water system to the well. The water mixes with detergents, corrosion inhibitors, the concentrated decontaminant, and other selected components in the well to form wash, decontaminant, or other solutions.

Preferably, the concentrated decontaminant and the other components are supplied in a disposable package or cup 44 which is positioned in the well 34 prior to a decontamination cycle. The cup 44 holds a measured dose of the concentrated decontaminant. optionally, a cleaner concentrate is also contained in the cup for forming a cleaning solution to clean the items prior to antimicrobial decontamination. The cup may include a number of compartments which separately contain the cleaning concentrate and decontaminant concentrate for separate release into the system. In this way, the items are first cleaned and then microbially decontaminated.

In a preferred embodiment, the cup holds a cleaning concentrate in a first compartment, components such as buffers for adjusting the pH, surfactants, chelating agents, and corrosion inhibitors for protecting the components of the system and items to be decontaminated from corrosion by the decontaminant in a second compartment, and a concentrated liquid peracetic acid solution (or reagents that react to form it) in a third compartment. A cup cutter 46, or other suitable opening member, is positioned at the base of the well 34 for opening selected compartments of the cup.

Alternatively, a solid or liquid concentrated decontaminant is supplied to the system from a separate bulk source (not shown), or is supplied to the system as the decontaminant solution, in an already-diluted form.

The water used for diluting the cleaner concentrate and decontaminant may be tap water or treated water, such as distilled water, filtered water, microbe free water, or the like. Alternatively, the water for diluting the cleaner concentrate and decontaminant concentrate is supplied from the sterile water generator B. The quantity of water entering the system is regulated to provide a decontaminant solution of a desired concentration in the decontamination chamber 12. The water is preferably passed through a microporous filter 50 in the water inlet line 42 which filters out particles of dirt and microorganisms. A valve 52 in the water inlet 42 closes when the selected quantity of water has been admitted.

A fluid supply pathway 60 connects the well 34, the pump 22, and the fluid distribution system 24. A heater 64, situated in the fluid supply pathway 60, heats the decontaminant solution and optionally the cleaning solution and rinse liquid to a preferred temperature(s) for effective cleaning, decontamination, and rinsing. A fluid return portion 66 of the pathway 60 returns the sprayed decontaminant solution from the sump 20. A recirculation valve 68 selectively returns used solution to the fluid supply line 60 and thence to the nozzles 16 and the fluid ports 18. Preferably, a return pump 70 pumps the sprayed decontaminant solution through the return fluid line 66, to be returned to the chamber 12.

Alternatively, the return pump is eliminated and the high pressure pump 22 circulates the decontaminant solution. At least a portion of the sprayed decontaminant solution is directed through the well 34 before being returned to the decontamination chamber. This ensures thorough mixing of the concentrated decontaminant and other components with the solution before returning the decontaminant solution to the nozzles 16, 18. Optionally, a detector 74 detects the concentration of one or more decontaminant, peracetic acid in the preferred embodiment, passing through the fluid lines. The detector may be an electrochemical monitoring system or a system employing conductivity measurements, chemical analysis, or the like.

A computer control system 80 controls the operation of the system A, including the pumps 22, 70, the heater 64, the valves 52, and the like. The control system 80 may control one or more additional systems A, if desired.

With reference also to FIG. 2, a source of water 102 supplies the sterile water generator B with water. The source of water preferably includes a hot water inlet line 102A and a cold water inlet line 102B which are connected with the respective hot and cold supplies of the house tap water supply system. Optionally, the water inlet line 42 is connected with the same water source as the cold water inlet line 102B for the sterile water generator. A sterile water delivery pathway or system C connects the sterile water generator B with the system A. A sterile water supply pathway C which is sterilized high temperature water in its liquid or vapor (steam) phase from the sterile water generator connects the sterile water generator B with the fluid supply line 60 of the system A.

A heat exchanger 110 is used to recover heat from the sterile water leaving the generator B. Specifically, the incoming unsterile water is fed through an interior passages 111 in the heat exchanger. Thermally sterilized, hot water is passed through the heat exchanger where it contacts outer surfaces of the passages 111. The incoming water is thus heated as the hot sterile water going through the downstream pathway C is cooled.

A mixing valve 112 in the upstream pathway receives the incoming tap water from the sources 102A and 102B. A controller 114 (which may be incorporated in the control system 80) receives temperature signals from a temperature detector 116 placed in the mixing valve, or elsewhere in the upstream pathway D. In one embodiment, the mixing valve 112 is self adjusting. In another embodiment, the controller 114 adjusts the mixing valve such that the water leaving the mixing valve is at or above a preselected minimum temperature (preferably around 30–35° C. This is done by adjusting the relative amounts of hot and cold tap water entering the mixing valve 112. If the mixing valve fails to establish the prescribed temperature, the controller adjusts other process variables described below to adapt for the colder or warmer incoming water.

The water is optionally passed from the mixing valve through one or more filters 120 which remove gross particles from the incoming water. Alternatively or additionally, the filters may be positioned in the sterile water delivery pathway C. Optionally, one or more of the filters includes a biofilter for removing undesired dissolved organic and inorganic materials and biological materials from the incoming tap water.

Preferably, a pump 122 adjusts the rate of water flow through the upstream line to a preselected level, preferably above the steam pressure for the operating temperature(s) selected to maintain the high temperature water in the generator in a liquid state. A pressure gauge 124 detects the pressure of the water flowing through the upstream line. The pressure gauge signals the controller which in turn controls the operation of the pump 122 and, if necessary, adjusts other process parameters. A one-way check valve 128 ensures that water does not flow in the reverse direction. The incoming water passes through the heat exchanger 110 and into a heating chamber or boiler 130. Instrumentation, such as pressure gauges and the like, which include dead-ended passages that are difficult to sterilize, are preferably connected to the upstream line rather than to the sterile water delivery pathway C.

Walls 132 of the heating chamber 130 are formed from a pressure resistant material, since the water in the heating chamber is preferably pressurized to above atmospheric pressure. A heating element or other suitable heater device 136 heats the water in a lower portion 137 of the boiler to a preselected temperature (preferably about 150° C.). One or more temperature detectors 138 detect the temperature of the water in the heating chamber. A water mixer insert 140 adjusts the flow pattern of the water flowing through the boiler. A heating element control 142 supplies electrical power to the heating element 136. On response to sensed temperature at the sensor 138, a solenoid valve 150 is pulsed on and off to maintain a minimum temperature resulting in automatic compensation for process changes such as heater 136 power, pump 122 flow rate and supply water temperature changes.

The incoming, unsterile water enters the heating chamber 130 adjacent a lower end thereof and progressively rises during heating such that a first in/first out flow path through the heating chamber is created. Mixing of heated and unheated water is minimized. The heating chamber preferably has a height to cross section aspect ratio which is large enough to provide the first in/first out fluid flow path through the heating chamber. The first in/first out system ensures that the water resides in the heating chamber for a preselected amount of time, allowing consistent control of the water sterilization process.

An upper portion of the heating chamber defines a residence time compartment 144. The heated water remains in the residence time compartment for a period of time sufficient for effective sterilization of the water to be completed. Thus, the sterilization of the water occurs both in the lower portion 137 of the heating chamber 130 and in the residence chamber 144. In one embodiment, the residence chamber is separate from the heating chamber. The residence time (the time the heated water remains in the residence chamber) is governed by the flow rate and residence chamber size. By selecting the temperature to which the water is heated within the heating chamber, the size of the residence chamber, and the flow rate of the incoming water, sterilization of the water can be assured.

While reference is made here to sterilization of the water by the sterile water generator, obviously, lesser forms of decontamination could alternatively be provided. For example, the water could be disinfected or pasteurized. Preferably, the water in the heating chamber 130 is maintained at a higher than atmospheric pressure so that it remains in the liquid state at the temperature to which it is heated. This allows higher temperatures above 100° C. to be used without the need for condensing steam.

A float gauge 152 in the heating chamber detects the level of the water in the heating chamber. In event that the water drops below a preselected level, the solenoid 150 switches off the heating element 136. Quick connects 154, 156 connect the heating chamber 130 to the up and downstream pathways for easy removal or attachment of the heating chamber.

Downstream, the sterile water passes from the residence chamber 144 to the heat exchanger 110. At this point, it has been thoroughly sterilized and can be reduced to a suitable temperature for rinsing (preferably around 50° C.). The heat exchanger 110 transfers heat from the sterile water to the incoming unsterile water through walls of the heat exchanger without the two flow paths coming in to direct fluid contact or otherwise undergoing fluid exchange. The cooled, sterile water passes along the pathway C to a first three-way solenoid valve 158 and thereafter to a second three-way solenoid valve 160 on its way to the circulation line 60. The two valves are sequentially adjusted during a thermal sterilization cycle so that a first portion 162 of the sterile pathway C, including the valves 158, 160, and a common pathway 164 are thermally sterilized prior to feeding the sterile water to the sterilization chamber 12. This ensures that the sterile water does not become recontaminated as it travels to the chamber.

Prior to supplying sterile rinse water from the sterile water generator B to the system A, the pathway first portion 162 is sterilized using high temperature water or steam generated by the heating chamber 130. During this thermal sterilization procedure, the solenoid valve 158 is switched so that the hot water or steam generated by the boiler travels from first portion 162 to the second valve 160 via the common line 164. The second valve 164 is switched to direct the water or steam along a drain line 174 to a drain 176. The three-way valves 158, 160 are positioned closely adjacent to minimize dead legs.

A check valve 178 in the drain line 174 prevents backflow from the drain into the sterile pathways. A steam thermostatic trap 180 discharges water and air from the lines when steam is used to sterilize connecting piping. A thermostatic trap automatically opens when excess water or air are in a steam line. This type of valve is open when water is being discharged through the valve. Cooling water or a heat sink dam may be used to reduce the temperature of the discharge to below temperatures as may be required by local code.

A pressure regulator 182 in the first portion 162 of the sterile water pathway may be adjusted to cause a back pressure in the boiler, which allows the development of high temperature water. Additionally, the solenoid valve 150 in the upstream line may be temporarily closed or restricted for a sufficient period to reduce the flow rate through the boiler. It is desirable to raise the temperature of the water in the heating chamber 130 to about 145° C., or above, to ensure that the water or steam generated is at a sufficient temperature for sterilizing the entire length of the sterile water delivery pathway C. The water is either boiled to create steam or raised to a sufficiently high temperature that it sterilizes the entire pathway C from the heating chamber through the second solenoid valve 160, including the heat exchanger 110. A temperature detector 184 connected with the first portion 162 of the pathway C detects the temperature of the high temperature, sterilizing water flowing through the pathway to determine if a preselected temperature for the line sterilization is achieved.

Once the thermal sterilization of the sterile water delivery path C is complete, the flow rate of water to the boiler may be increased and the temperature of the water in the boiler reduced to a suitable temperature for sterilization of the flowing water.

Optionally, a sampling port 200 is connected in the drain line between the second three-way valve 160 and the check valve 178. The sampling port provides a port at which the generated water can be tested to insure that it meets quality standards. The sample port includes a sterile barb 202 which is enclosed in a housing 204. During the thermal sterilization step, the high temperature water or steam passes through the sterile barb and the housing before leaving the system through the drain. In this manner, the sterile barb 202 is sterilized with each cycle. After the thermal sterilization step has been completed and the sterile water generator is ready to supply cooler sterile water, the housing 204 is disconnected and a sampling container is connected with the sterile barb 202. To sample the sterile water, the three-way valves 158 and 160 are switched to the position of FIG. 2 for a sufficient duration to allow the sterile water to fill the container. Optionally, the housing 204 also includes a porous, microbe shielding filter 206.

Figure 3:
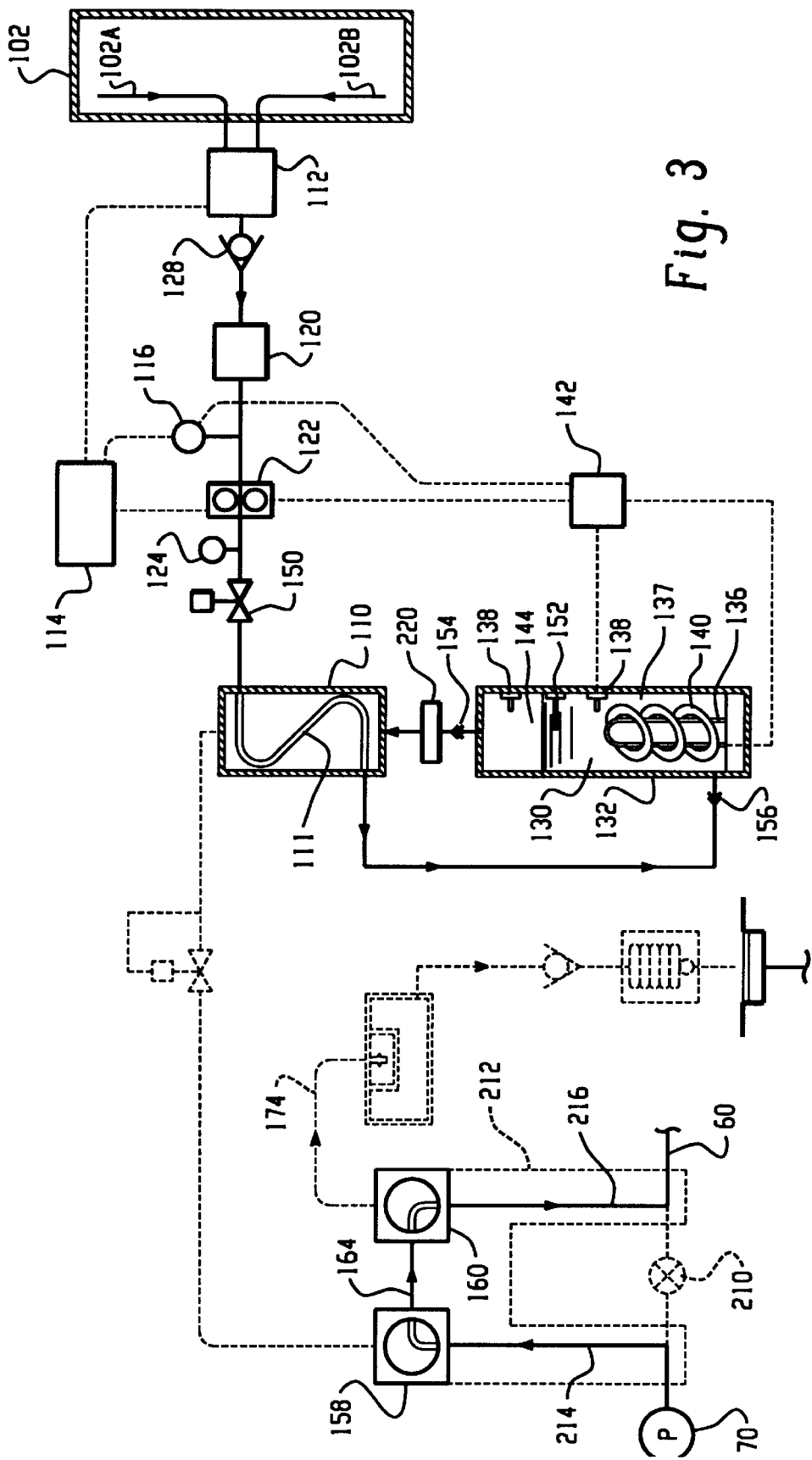
FIG. 3 shows the plumbing diagram of FIG. 2, configured for low temperature liquid sterilization of a portion of internal fluid pathways.

With reference to FIG. 3, during a chemical, second sterilization step, the position of three-way valves 158 and 160 is switched. A valve 210 in circulation line 60 is closed to force the chemical sterilant to flow through and sterilize a second portion 212 of the pathway C including the three-way valve 158, the common path 164, the three-way valve 160, and leg segments 214 and 216. The chemical sterilant flows through this path for a sufficient time to sterilize or disinfect the second portion of the sterile water delivery system C and the items in the sterilization chamber 12. During the chemical sterilization step, the temperature of the sterile water is reduced to the desired delivery temperature, preferably about 55° C. or less. In this way, sterile rinse water can begin being pumped into the system A as soon as the decontamination portion of the cycle is complete. Preferably, the first and second sterilization phases occur with every use of the system A to ensure that the rinse water entering the system passes along a fully sterilized sterile water delivery system C.

Figure 4:
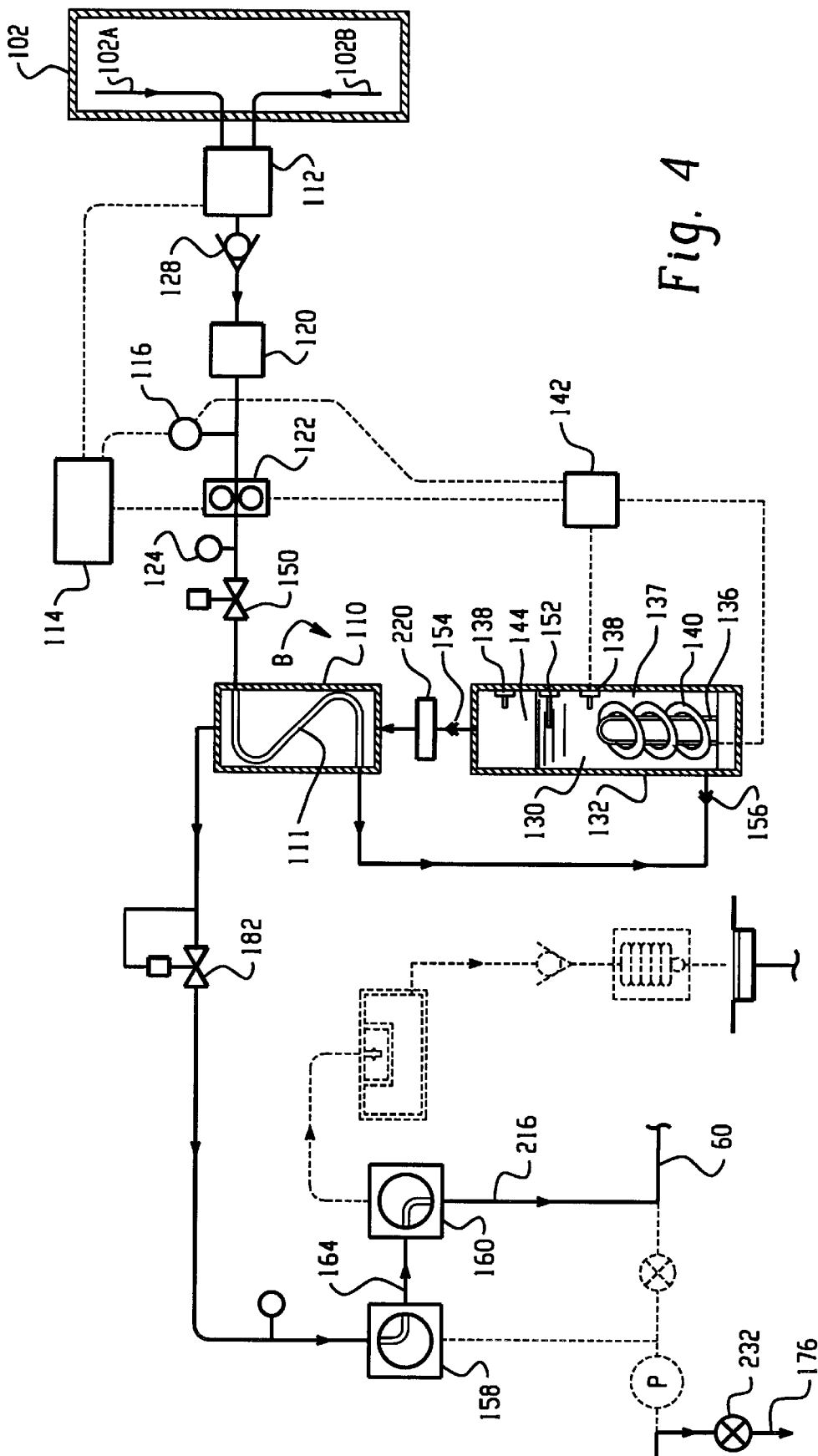
FIG. 4 shows the plumbing diagram of FIG. 2, configured for delivery of sterile water.

When sterile water is required by the system A, the three-way valves 158 and 160 are positioned as shown in FIG. 4. The sterile water flows from pathway first portion 106 through valves 158, 160, the common leg 164 and connecting leg 214 into the system A.

As can be seen, the entire length of the pathway C between the heating chamber 130 and the system A is sterilized prior to the rinse stage of each cycle so that the rinse water is not contaminated inadvertently by microorganisms which may have collected along the pathway or in the heat exchanger between decontamination cycles or when the pathway is disconnected from the sterilizer.

In another embodiment, water heated by the heating chamber is used to back flush and sterilize the upstream water line from the heater 130 to the inlet 102. This is preferably performed periodically to prevent a buildup of microorganisms in the water inlet line. This is of particular importance, for example, where one of the filters 120 is a biofilter. In this embodiment, the check valve 128 is replaced by a valve which selectively permits the water to flow backwards along the line towards the mixing valve 112.

The sterile water generator B is capable of generating a continuous flow of sterile water for a variety of purposes. For supplying rinse water to the system A, the generator B preferably generates a flow of rinse water of from about 2 to 10 liters per minute with a preferred flow rate of about 4 liters per minute. The heating chamber preferably heats the water to a temperature of about 130–145° C., or above. For flow rate of 4 liters per minute and a temperature leaving the heating chamber 130 of about 130–145° C., the residence chamber 144 of about 2 liters holds the water for a sufficient period for sterilization.

The water heater precipitates water hardness salts in the heat exchanger 111 and the heating compartment 130. This reduces build up of such salts on the surface of the heat exchanger 110 or in system A. These salts are continuously removed from the system during routine processing.

Optionally, a filter 220 in the sterile water delivery pathway C collects precipitated salts which have not been removed by the. chamber 130. The filter is prefereably removed periodically and cleaned or replaced.

Precipitation of negative solubility coefficient salts, such as calcium and magnesium carbonate, has an additional benefit in that the precipitate entrains low molecular weight endotoxins (3000 to 6000 Daltons) which are otherwise difficult to remove with conventional filtration systems. The endotoxins form during the destruction of Gram negative bacteria and other organisms in the incoming water. Removing these endotoxins with the precipitating salts increases the purity of the sterile water.

Optionally, additional salts, such as calcium and magnesium carbonate, are added, in solution, to the incoming water. These salts increase the amount of precipitating salts and further increase the removal of endotoxins from the sterilized water. The salt precipitate with the entrained endotoxins is removed in the chamber 130 or by the filter 220.

In a typical decontamination cycle, items to be decontaminated are first inserted into the cabinet 10 through the door 14, and the door is closed. A fresh cup 44 of concentrated decontaminant and other components is inserted into the well 34 and a restraining member or lid 230 positioned over the cup. The opening member 46 opens the cleaner compartment of the cup. The computer control 80 signals the valve 52 in the water inlet line 42 to open, allowing water to circulate through the well and the fluid lines 60 and 66. The decontaminant concentrate mixes with the water and is delivered by the pump 22 under pressure to the nozzles 16 and endoscope connection ports 18. The nozzles spray the decontaminant solution over the outer surfaces of the items while the connection ports deliver the solution to the internal passages, thereby decontaminating inner and outer surfaces simultaneously. Sprayed decontaminant solution which drips off the items is collected in the sump 20. The return pump 70 returns the collected solution from the sump to the fluid supply line 60, preferably after first passing a part of the collected solution through the well 34 to ensure complete mixing of the concentrated decontaminant in the solution.

Prior to the decontaminating portion of the cycle, the sterile water generator is activated (FIG. 2) and the first portion 162 of sterile water delivery pathway, valves 158, 160 and the common passage 164 are sterilized or microbially decontaminated with hot water or steam, as described above.

During the liquid contamination portion of the cycle (FIG. 3), the decontaminant solution also passes through the valves 158 and 160 and the common passage to decontaminate the legs 214 and 216.

After a period of circulation of the decontaminant solution or solutions sufficient to effect decontamination of the items, a drain valve 232 in the system A is opened and the decontaminant solution flushed from the system A to the drain. The solenoid valves 158, 160 are positioned (FIG. 4) so that they supply sterile rinse water from the sterile water generator B along the now sterile pathway C. The rinse water passes through the inlet 54 into the supply line 60 and to the nozzle fittings 16 and connection ports 18 in the decontamination chamber 12. The sterile rinse water flows over the inner and outer surfaces of the decontaminated items to rinse traces of the decontaminant solution and dirt or other contaminants from the items. The rinse water drips off the items into the sump 20 and is directed to the drain along line 66. The drain valve 232 is opened so that the sprayed rinse water flows to the drain 176.

Optionally, an air line 240 supplies a source of microbe-free air to the system to blow out lumens and remove excess water from the decontaminated items. The air is preferably passed through a microbial filter 242 before entering the system.

After rinsing and optionally drying the items, the items are removed from the decontamination chamber 12 for immediate use or transferred to sterile pouches and stored until needed.

Figure 5:
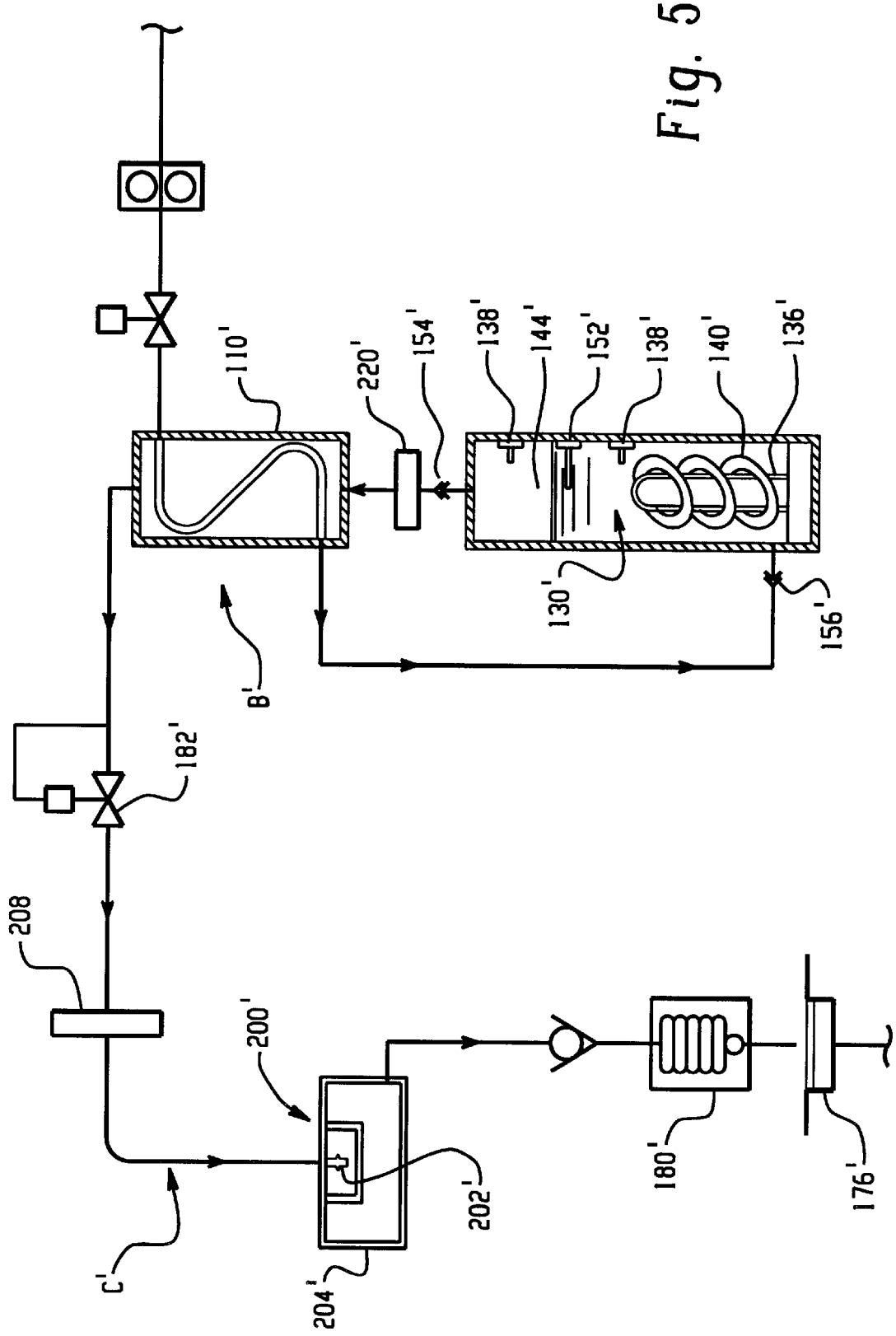
FIG. 5 is a plumbing diagram of a sterile water generator configured for supply of sterile water from a sterile barb.

With reference to FIG. 5, an alternative embodiment of a sterile water generator B' is used to supply sterile water on demand through a sterile pathway C'. The generator is similar in many respects to the generator B of FIGS. 2–4. Like parts are numbered with a prime ('). The sterile water generator B' includes a boiler 130' and heat exchanger 110', as for the generator B of FIGS. 2–4. An upstream pathway supplies unsterile water, such as tap water, to the boiler. In this embodiment, the valves 158 and 160 are omitted and the sterile water is directed from the heat exchanger to a sample port 200'. Sterile water is obtained, as needed from a sterile barb 202' in a compartment 204'. IV bags, or other containers to be filled, are connected directly to the barb.

Optionally, a nanofilter 208 is positioned in the sterile water delivery pathway C', between the heat exchanger 110' and the compartment 200'. The filter 208 is used to remove minute particles of nanometer dimensions, such as endotoxins, from the sterile water. The resulting endotoxin-free water is of water for injection (WFI) quality. The nanofilter is preferable sterilized in place, during pre-sterilization of the line C'. As for the generator B of FIGS. 2–4, the boiler 130' is used to generate high temperature water or steam which is flowed along the sterile pathway C' and through the compartment to a thermostatic trap 180' and a drain 176'. The sterilization fluid (water or steam) passes through the nanofilter 204' and the sterile barb 202' during this step. Once the line has been pre-sterilized, the boiler reverts to generation of sterile water, which flows along the sterile pathway C' to the barb, where it is accessed as needed.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sterile water generator comprising:
   a water heater which receives incoming water and heats the water to a sufficient temperature to sterilize the water;
   a presterilized water delivery pathway passing through a heat exchange for delivering the sterile water from the water heater to a rinse water inlet to a low temperature sterilizer in which the sterile water is to be used, the presterilized pathway being sterilized along at least a first portion of its length by heated water or steam from the water heater;
   means for chemically sterilizing a second portion of the length of the water delivery pathway;

a control for controlling at least the water heater and a flow of cooling water through the heat exchanger to first thermally sterilize the presterilized water pathway and then supply low temperature sterile water through the presterilized water pathway to the rinse water inlet of the low temperature sterilizer.

2. The A sterile water generator comprising:

a water heater which receives incoming water and heats the water to a sufficient temperature to sterilize the water;

a presterilized water delivery pathway passing through a heat exchange for delivering the sterile water from the water heater to a rinse water inlet to a low temperature sterilizer in which the sterile water is to be used, the presterilized pathway being sterilized along at least a portion of its length by heated water or steam from the water heater;

a first valve, the first valve having first and second positions:

(a) in the first position the first valve connects the presterilized water delivery pathway with the site; and (b) in a second position the first valve connects the presterilized water delivery pathway with a drain line, for passing a thermal sterilization fluid through the presterilized water delivery pathway to the drain line; and a control for controlling at least the water heater and a flow of cooling water through the heat exchanger to first thermally sterilize the presterilized water pathway and then supply low temperature sterile water through the presterilized water pathway to the rinse water inlet of the low temperature sterilizer.

3. A sterile water generator comprising:

a water heater which receives incoming water and heats the water to a sufficient temperature to sterilize the water;

a sterile water delivery pathway for delivering the sterile water from the water heater to a site at which the sterile water is to be used, the sterile pathway being presterilized along at least a portion of its length by heated water or steam from the water heater;

a first valve, the first valve having first and second positions:

a) in the first position the first valve connects the sterile water delivery pathway with the site; and b) in a second position the first valve connects the sterile water delivery pathway with a drain line, for passing a thermal sterilization fluid through the sterile water delivery pathway to the drain line; and a second valve, the second valve having first and second positions:

a) in the first position, the second valve connects the water heater with the first valve, allowing sterile water to flow through the sterile water delivery pathway to the site when the first valve is in the first position;

b) in the second position, the second valve connects a source of a decontamination fluid with the first valve for sterilizing a portion of the sterile water delivery pathway between the first valve and the site when the first valve is in the second position.

4. The sterile water generator of claim 1, further including a residence time chamber which is dimensioned to retain the water heated by the water heater for a sufficient time for sterilization of the water prior to passing the sterile water through the heat exchanger.

5. The sterile water generator of claim 4, wherein the residence time chamber is integral with the water heater.

6. The sterile water generator of claim 1, further including a filter in the presterilized water delivery pathway for filtering precipitated salts and entrained endotoxins from the sterile water.

7. A sterile water generator comprising:

a water heater which receives incoming water and heats the water to a sufficient temperature to sterilize the water;

a sterile water delivery pathway for delivering the sterile water from the water heater to a site at which the sterile water is to be used, the sterile water delivery pathway being presterilized along at least a first portion of its length by heated water or steam from the water heater, a second portion of the sterile water delivery pathway being chemically presterilized; and a sterile sample port for obtaining a sample of the sterile water.

8. The sterile water generator of claim 1, wherein the presterilized water delivery pathway includes a temperature detector for ensuring that water passing through the presterilized water delivery pathway during a pathway sterilization step is at a sufficient temperature for sterilizing the presterilized water delivery pathway.

9. A method of supplying sterile water through a sterile fluid delivery pathway, the method comprising:

a) heating a liquid to generate a first thermal sterilizing fluid;

b) passing the first sterilizing fluid along at least a first portion of a sterile fluid delivery pathway to effect thermal sterilization of the first portion of the pathway;

c) passing a second sterilizing fluid along a second portion of the sterile fluid delivery pathway to effect sterilization of the second pathway portion, the first and second portions each having (1) at least one common portion over which both the first and second sterilizing fluids are passed and (2) a non-common portion over which only one of the first and second sterilizing fluids pass;

d) generating sterile water by heating water; and e) passing the sterile water along the sterilized sterile fluid delivery pathway.

10. A method of supplying sterile water through a sterile fluid delivery pathway, the method comprising:

a) passing a first sterilizing fluid along a first portion of a sterile fluid delivery pathway to effect sterilization of the first portion of the pathway, the first sterilizing fluid being one of hot water and steam;

b) passing a second sterilizing fluid along a second portion of the sterile fluid delivery pathway to effect sterilization of the second pathway portion, the second sterilizing fluid including an antimicrobial liquid selected from the group consisting of peracetic acid and hydrogen peroxide, the first and second portions being non-coextensive;

c) steps (a) and (b) being performed non-concurrently such that the sterile pathway is in part thermally sterilized and in part chemically sterilized; and d) passing sterile water along the sterilized sterile fluid delivery pathway.

11. The method of claim 9, wherein step a) includes: maintaining the first sterilizing fluid at an above atmospheric pressure.

12. The method of claim 9, wherein step c) includes sterilizing the second portion of the fluid pathway by passing an antimicrobial liquid along the second portion of the pathway.

13. The method of claim 12 further including;
discarding the antimicrobial liquid that has passed over the second passageway portion.

14. The method of claim 12, wherein the antimicrobial liquid is selected from the group consisting of peracetic acid and hydrogen peroxide.

15. The method of claim 9, wherein step c) includes:
passing a portion of the first sterilizing fluid through a sample port to sterilize the sample port.

16. A method of supplying sterile water through a sterile fluid delivery pathway, the method comprising:
sterilizing a fluid delivery pathway including:
passing heated water or steam along at least a first portion of a the fluid delivery pathway to effect sterilization of the first portion of the pathway;
discharging the heated water or steam before it reaches a second portion of the pathway;
passing sterile water along the sterilized fluid delivery pathway;
entraining endotoxins in the sterile water with precipitating salts; and
filtering the precipitating salts and endotoxins from the sterile water.

17. The method of claim 16, wherein the step of filtering the precipitating salts includes passing the sterile water through a filter and wherein step b) further includes:
sterilizing the filter.

18. A method of decontamination comprising:
sterilizing at least a portion of a rinse fluid delivery pathway with heated water or steam;
contacting items to be decontaminated with a decontaminant fluid;
sterilizing at least a remaining portion of the rinse fluid pathway with the decontaminant fluid which decontaminates the items; and
passing rinse fluid through the rinse fluid pathway and contacting the decontaminated items with the rinse fluid.

19. The method of claim 18, wherein the flowing step further includes:
cooling the rinse fluid with cold water received for heating.

20. A decontamination system comprising:
a vessel for receiving items to be sterilized;
a source of an antimicrobial agent connected with the vessel which supplies the antimicrobial agent to the vessel for decontaminating the items in the vessel; and
a thermal sterile water generator connected with the vessel by a sterile water delivery pathway which supplies sterile rinse water to the vessel for rinsing the decontaminated items, only a portion of the sterile water delivery pathway being sterilized with heated water from the thermal sterile water generator.

21. The system of claim 20, further including:
an antimicrobial agent reservoir;
a fluid flow loop through which the antimicrobial agent flows from the antimicrobial agent reservoir to the vessel and from the vessel back to the reservoir;
a source of the antimicrobial agent connected with at least one of the fluid flow loop and the reservoir; and
a water inlet connected with the fluid flow loop upstream of the vessel, the thermal sterile water generator being connected to the water inlet to supply sterile rinse water thereto.

22. The system of claims 20, further including:
a means other than the heated water from the thermal sterile water generator for sterilizing the portion of the sterile water delivery pathway left unsterilized by the heated water.

* * * * *